United States Patent [19]

Dubas et al.

[11] Patent Number: 4,482,463

[45] Date of Patent: Nov. 13, 1984

[54] LUBRICANT COMPOSITIONS CONTAINING NITROGEN-CONTAINING POLYSULFIDE LOAD-CARRYING ADDITIVES

[75] Inventors: Henri Dubas, Ettingen; Rudolf Kirchmayr, Aesch, both of Switzerland

[73] Assignee: Ciba-Geigy Corporation, Ardsley, N.Y.

[21] Appl. No.: 422,329

[22] Filed: Sep. 23, 1982

[30] Foreign Application Priority Data

Oct. 6, 1981 [CH] Switzerland ............... 6416/81

[51] Int. Cl.³ .................................................. C10M 1/38
[52] U.S. Cl. .................................... 252/47.5; 252/47
[58] Field of Search .................................. 252/47, 47.5

[56] References Cited

U.S. PATENT DOCUMENTS

| | | | |
|---|---|---|---|
| 2,351,657 | 6/1944 | Bayes | 252/47.5 X |
| 2,364,122 | 12/1944 | Bayes | 252/47.5 X |
| 2,598,333 | 5/1952 | Zerbe | 252/47 X |
| 2,648,673 | 8/1953 | Lesslie | 252/47 X |
| 3,251,811 | 5/1966 | Warner et al. | 252/47 X |
| 3,577,459 | 5/1971 | Laughlin | 252/47 X |
| 4,039,552 | 8/1977 | Brois et al. | 252/47 X |
| 4,110,234 | 8/1978 | Loveless et al. | 252/47 X |

*Primary Examiner*—Andrew Metz
*Attorney, Agent, or Firm*—Luther A. R. Hall

[57] ABSTRACT

The invention relates to lubricant compositions containing
(a) a mineral and/or synthetic base oil,
(b) a compound of the formula I $$A—(S)_n—G \qquad (I)$$

wherein n is preferably 2 and A and G are the same or different and represent either a radical

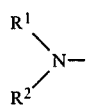

wherein $R^1$ and $R^2$ may be methyl, or are a nitrogen-containing 5- to 7-membered heterocyclic radical such as

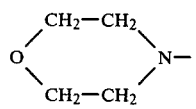

and (c) optionally further additives.

11 Claims, No Drawings

LUBRICANT COMPOSITIONS CONTAINING NITROGEN-CONTAINING POLYSULFIDE LOAD-CARRYING ADDITIVES

The present invention relates to the use of polysulfides which contain 2 N-atoms, as lubricant additives.

It is customary to add different additives to mineral and synthetic lubricants in order to improve their performance properties. In particular, there is a need to provide additives which protect the devices which it is desired to lubricate from wear. The requirment made of these wear inhibitors is that they shall increase the load-carrying capacity of the lubricant and not have a corrosive action on the metal parts to be protected. Known lubricant additives are sulfurised sperm oil and sulfurised olefins, e.g. as disclosed in German Offenlegungsschrift specifications Nos. 2 166 893 and 2 606 101. The extreme pressure properties of lubricants which contain such additives are often unsatisfactory. In particular, the heat stability is insufficient and copper and iron are attacked by corrosion.

It is the object of the present invention to provide lubricant systems which do not have the shortcomings of the known systems referred to above.

Accordingly, the present invention provides lubricant compositions which contain (a) a mineral and/or synthetic base oil,
(b) one or more compounds of the formula I $$A\text{—}(S)_n\text{—}G$$

(I)

where n is an integer from 2 to 6 and A and G are the same or different and represent

wherein $R^1$ and $R^2$ are the same or different and are straight chain or branched $C_1\text{-}C_{24}$alkyl, $C_3\text{-}C_{18}$alkenyl, $C_3\text{-}C_{12}$cycloalkyl or aryl containing 6 to 10 carbon atoms in the nucleus, or $C_7\text{-}C_{30}$aralkyl, each unsubstituted or substituted by —Cl, —$ZR^5$, —ZCN, —NCZ, $CZZ^1R^5$, —$CZNR^7R^8$, —$NR^7R^8$ or —$CZZ^1E$, each of Z and $Z^1$ independently of the other is —O—, —S—, —$S_2$, —SO—, —$SO_2$, or —$SO_3$, $R_5$ is hydrogen or $C_1\text{-}C_{18}$alkyl or $C_3\text{-}C_{18}$alkenyl, each unsubstituted or substituted by —Cl, —ZCN, —NCZ or —CN, and E is Na, K or —$NR^7R^8R^9$, in which $R^7$ to $R^9$ are as defined for $R^5$ and may be the same or different; or wherein A and/or G are a heterocyclic radial containing 5 to 12 ring members and the nucleus of which is saturated or unsaturated and contains a N-atom as the atom linking it to the —$(S)_n$— group, which radial may additionally contain —O—, —S—or a second N-atom as heteroatom and may be substituted in the nucleus up to 4 times by $R_1$ and $R_2$; and (c) optionally further lubricant additives, the base oil (a) containing 0.001 to 5% by weight, based on said oil, of the compound of formula I.

$R^1$ and $R^2$ as alkyl radicals may be methyl, isopropyl, n-butyl, sec-butyl, tert-butyl, tert-amyl, 2-ethylhexyl, n-octyl, tert-octyl, n-dodecyl, 1,1,7,7-tetramethyloctyl, n-octydecyl, with 2-ethylhexyl being preferred.

$R^1$ and $R^2$ as cycloalkyl may be cyclopropyl, cyclopentyl, cyclohexyl, cycloheptyl, cyclooctyl or cyclododecyl, with cyclopentyl and cyclohexyl being preferred.

$R^1$ and $R^2$ as aralkyl may be benzyl, phenylethyl and 2-phenyl-isopropyl.

$R^1$ and $R^2$ as alkaryl may be tolyl, xylyl, 2,6-diethylphenyl or 4-tert-butylphenyl.

$R^1$ and $R^2$ as aryl may be phenyl, α-naphthyl or β-naphthyl.

A heterocyclic radical represented by A and/or G may be morpholino, piperazino, piperidino, pyrrolidino, hexamethyleneimino, imidazolidino, imidazo or pyrrolo.

Eligible substituents of the above groups $R^1$ and $R^2$ or of the heterocyclic radicals A and/or G may be: methyl, ethyl, isopropyl, n-butyl, vinyl, allyl, chlorine, mercapto, methylthio, methylsulfoxido, dodecylthio, dodecyldithio, sulfo, sulfonato, sulfamoyl, methoxysulfinyl, hydroxy, methoxy, ethoxy, allyloxy, n-octyloxy, 3,6,9,12,15-pentaoxa-heptadecyloxy, cyano, cyanato, thiocyanato, isothiocyanato, methoxycarbonyl, isooctyloxycarbonyl, carboxy, sodiumcarboxylato, acetoxy, 2-ethylhexanoyloxy, butanoyl, dimethylamino, bis-(2,2')dihydroxyethylamino, didodecylamino. It will be understood that the above list of substituents is not to be construed as in any way constituting a restriction of the invention.

Preferred lubricant compositions are those which contain compounds (b) of the formula I, wherein A and G are the same or different and represent

wherein $R^1$ and $R^2$ are the same or different and are straight chain or branched $C_1\text{-}C_{24}$alkyl which is unsubstituted or substituted by —Cl,—$ZR^5$, —ZCN, —NCZ, —$CZZ^1R^5$, —$ZCZ^1R^5$, —$CZNR^7R^8$, —$NR^7R^8$ or -13 $CZZ^1E$, with the proviso that, if only A has the meaning given above, G is a 5- to 12-membered heterocyclic radical as previously defined above.

Preferred lubricant compositions are also those which contain compounds (b) of the formula I, wherein A and G are the same or different and represent

wherein $R^1$ and $R^2$ are the same or different and, in the same way as $R^5$, represent straight chain or branched $C_1\text{-}C_{18}$alkyl which is unsubstituted or substituted by —Cl, —$ZR^5$, ZCN, —NCZ, —$CZZ^1R^5$, $NR^7R^8$, —$ZCZ^1R^5$, —$CZNR^7R^8$ or —$CZZ^1E$, with the proviso that, if only A has the meaning given above, G is a 5- to 12-membered heterocyclic radial as previously defined above.

Further preferred lubricant compositions are those which contain compounds (b) of the formula I, wherein A and G are the same or different and are morpholino, with the proviso that, if only A has the meaning given above, G represents

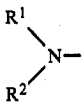

wherein $R^1$ and $R^2$ have any of the meanings given above.

Yet further preferred lubricant compositions are those which contain compounds (b) of the formula I, wherein n is 2.

The following three lubricant compositions are particularly preferred embodiments of the invention:

1. Lubricant compositions which contain those compounds (b) of the formula I, wherein A and G are the same or different and represent

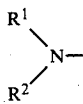

wherein $R^1$ and $R^2$ are the same or different and are straight chain or branched, unsubstituted $C_1$-$C_{18}$ alkyl.

2. Lubricant compositions which contain those compounds (b) of the formula I, wherein A and G represent

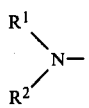

wherein $R^1$ and $R^2$ are identical radicals and represent $C_5$-$C_{15}$ alkyl.

3. Lubricant compositions which contain those compounds (b) of the formula I, wherein A and G are the same and represent an identical 5- to 12-membered heterocyclic radical as previously defined above.

The compounds of the formula I employed in the practice of this invention are known and described as vulcanising agents and accelerators for the vulcanisation of rubber in U.S. Pat. No. 3,359,247. They are prepared by known methods which need not be here described in detail. For example, a secondary amine may be reacted with sulfur chloride and a base, in the molar ratio of 2:1:2, in a solvent.

Examples of compounds of the formula I are:
1. bis-(diisooctylamino)-disulfide
2. bis-(dicyclohexylamino)-disulfide
3. dimorpholino-disulfide
4. bis-(N-phenyl-N-ethylamino)-disulfide
5. $[CH_3CH_2—(OCH_2CH_2)_5]_2$ —N—S—S—N—$[(CH_2CH_2O)_5CH_2CH_3]_2$
6. $(H_{25}C_{12}SCH_2CH_2)_2N$—S—S—N—$(CH_2CH_2SC_{12}H_{15})_2$ 7. 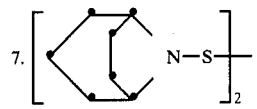

8. bis-(N-2-ethylehexyl-N-2-cyanoethylamino)-disulfide
9. bis-(di-2-acetoxyethylamino)-disulfide
10. bis-(2-trichloromethoxycarbonylpyrrolidino)-disulfide
11. bis-(di-p-methylpiperazino)-disulfide
12. bis-(dipiperidino)-disulfide
13. bis-(dicyclohexylamino)-tetrasulfide
14. (dicyclohexylaminomorpholino)-disulfide
15. dithio-tetra-n-butyl bis-(iminodiacetate).

The further lubricant additives (c) which may be added, if desired, to the lubricant composition in order to improve certain performance properties, are preferably antioxidants, metal deactivators, rust inhibitors, viscosity index improvers, pour-point depressors, and dispersants/detergents.

Examples of antioxidants are:

(a) Alkylated and non-alkylated aromatic amines and mixtures thereof, for example: dioctyldiphenylamine, mono-tert-octylphenyl-α- and -β-naphthylamines, phenotriazine, dioctylphenothiazine, phenyl-α-naphthylamine, N,N'-di-sec-butyl-p-phenylenediamine.

(b) Sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol), 4,4'-methylene-bis-(2,6-di-tert-butylphenol).

(c) Alkyl-, aryl- or alkarylphosphites, for example: trinonylphosphite, triphenylphosphite, diphenyldecylphosphite.

(d) Esters of thiodipropionic acid or thiodiacetic acid, for example: dilaurylthiodipropionate or dioctylthiodiacetate.

(e) Salts of carbamic and dithiophosphoric acids, for example: antimony diamyldithiocarbamate, zinc diamyldithiophosphate.

(f) A combination of two or more of the above antioxidants, for example: an alkylated amine and a sterically hindered phenol.

Examples of metal deactivators are:

(a) for copper, e.g.: benzotriazole, tetrahydrobenzotriazole, 2-mercaptobenzotriazole, 2,5-dimercaptothiadiazole, salicyclidene propylenediamine, salts of salicylaminoguanidine.

(b) for lead, e.g.: sebacic acid derivatives, quinizarine, propyl gallate.

(c) A combination of two or more of the above additives.

Examples of rust inhibitors are:

(a) Organic acids, the esters, metal salts and anhydrides thereof, e.g.: N-oleyl sarcosine, sorbitan monooleate, lead naphthenate, dodecenylsuccinic anhydride.

(b) Nitrogen-containing compounds, for example:
I. Primary, secondary or tertiary aliphatic or cycloaliphatic amines and amine salts of organic and inorganic acids, for example oil-soluble alkylammonium carboxylates.
II. Heterocyclic compounds, e.g. substituted imidazolines and oxazolines.

(c) Phosphorus-containing compounds, for example: amine salts of phosphoric acid partial esters.

(d) Sulfur-containing compounds, for example: barium dinonylnaphthalenesulfonates, calcium petroleum sulfonates.

(e) Combinations of two or more of the above additives.

Examples of viscosity index improves are: polymethacrylates, vinyl pyrrolidone/methacrylate copolymers, polybutene, olefin copolymers, styrene/acrylate copolymers.

Examples of pour-point depressors are: alkylated naphthalenes, alkylated phenols, polymethacrylates.

Examples of detergents and dispersants are: polyalkenylsuccinimides, oil-soluble metal soaps such as calcium, barium, magnesium and aluminium carboxylates, phenolates or sulfonates.

Examples of other wear resisting additives are: Compounds containing sulfur and/or phosphorus and/or halogen, e.g. sulfurised vegetable oils, zinc dialkyl dithiophosphates, tritolylphosphate, chlorinated paraffins, alkyl and aryl disulfides. The concentration of the further lubricant additives (c) in the lubricant compositions of the invention varies greatly, depending on which type is employed. However, these concentrations are very well known to the skilled person, so that specific details of them may be dispensed with.

The use of compounds of the formula I as lubricant additives also constitutes a further object of the invention.

If several compounds of the formula I are used simultaneously, these compounds are added to the base oil singly or in admixture.

The compounds of formula I are effective extreme pressure additives for lubricants even when used in very insignificant amounts. Thus mineral and synthetic lubricating oils, and mixtures thereof, to which 0.001 to 5% by weight, preferably 0.02% to 3% by weight, based on the lubricant, of a compound of formula I has been added, have excellent extreme pressure lubricating properties, which are observed in greatly reduced wear and tear of the rubbing surfaces to be lubricated. The suitable lubricating oils are known to the skilled person and are described e.g. in "Schmiermittel Taschenbuch" (Hüthig Verlag, Heidelberg, 1974 ). The invention is illustrated by the following Examples.

EXAMPLES

The products are prepared in a manner corresponding to that described below for additive 1. Parts are by weight and the numbers of the compounds are in accordance with the particulars given in the description on pages 6 and 7.

Preparation of additive 1 of formula I 10 parts of diisooctylamine are added to 67 parts of ether and to this mixture are added first over 50 minutes, at 1°-3° C., half of a solution of 28 parts of sulfur chloride in 10 parts of ether and then 3 parts by volume of a 25% aqueous solution of sodium hydroxide. The remainder of the sulfur chloride solution and another 3 parts by volume of 25% aqueous solution of sodium hydroxide are then added simultaneously over 40 minutes at 1°-3° C. After separation of the aqueous phase, the organic phase is washed with 25 parts of water in 3 portions, then dried and concentrated, giving 11 parts of a yellow oil.

Examples 1 to 5

5 lubricant compositions are tested by the Tentative Method IP 239/69 (extreme pressure and wear lubricant test for oils and greases, four-ball machine) using the Shell four-ball apparatus. The results are summarised in Table 1.

TABLE 1

| Example | Base oil (a) | Additive (b) of the formula I | Concentration (% by weight) | ISL (kg) | WL (kg) | WSD (mm) |
|---|---|---|---|---|---|---|
| 1 | Vitrea 41 ® | without | — | 60 | 145 | 1.2 |
| 2 | Vitrea 41 ® | 1 | 1% | 70 | 240 | 0.5 |
| 3 | Vitrea 41 ® | 2 | 1% | — | 240 | 0.5 |
| 4 | Vitrea 41 ® | 3 | 1% | 80 | 300 | 0.5 |
| 5 | Vitrea 41 ® | 4 | 1% | — | 240 | 0.5 |
| 6 | Vitrea 41 ® | 8 | 1% | 80 | 240 | 0.5 |
| 7 | Vitrea 41 ® | 11 | 1% | — | 260 | 0.5 |
| 8 | Vitrea 41 ® | 12 | 1% | — | 300 | 0.6 |
| 9 | Vitrea 41 ® | 15 | 1% | — | 220 | 0.5 |

ISL = initial seizure load: the load at which the oil film breaks up within 10 seconds WL = weld load: the load at which the 4 balls become welded within 10 seconds WSD = wear scar diameter: the average wear diameter at a load of 40 kg over 1 hour.

Vitrea 41 ® is a base oil available from Shell.

Example 10

A commerical mixture of primary amines, available from Rohm & Haas under the registered trademark PRIMENE ® 81-R, is reacted at elevated temperature with acrylonitrile to give a mixture of secondary amines. This product is then reacted with sulfur chloride. The conditions are the same as those described for the preparation of additive 1 of formula I, except that a petroleum distillate is used as solvent. Using the Shell four-ball apparatus, the following results are obtained:

additive concentration: 1%
base oil: Vitrea 41 ®
ISL: 80 kg
WL: 220 kg
WSD: 0.5 mm Example The corrosiveness of Vitrea 41 ® which contains 1% by weight of additive 1 is determined in accordance with DIN 51 585. Result: corrosion 0–1, i.e. no corrosion.

What is claimed is:

1. A lubricant composition which comprises
   (a) a mineral oil, a synthetic oil or mixture thereof, and
   (b) 0.001 to 5% by weight, based on the lubricant, of one or more compounds of formula I $$A-(S)_n-G \quad (I)$$

wherein n is an integer from 2 to 6, and
A and G are the same or different and represent

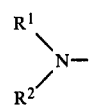

wherein $R_1$ and $R_2$ are the same or different and are $C_1-C_{24}$ alkyl, $C_3-C_{18}$ alkenyl, $C_3-C_{12}$ cycloalkyl, aryl containing 6 to 10 carbon atoms in the nucleus, $C_7-C_{30}$ aralkyl, or said alkyl, said alkenyl, said cycloalkyl, said aryl or said aralkyl substituted by —Cl, by —$ZR^5$, by —ZCN, by —NCZ, by $CZZ^1R^5$, by —$ZCZ^1R^5$, by —$CZNR^7R^8$, by —NR $R^8$ or by —$CZZ^1E$, where Z and $Z^1$ are independently —O—, —S—, —$S_2$, —SO—, —$SO_2$— or —$SO_3$—, $R^5$ is hydrogen, $C_1$-$C_{18}$ alkyl, $C_3$-$C_{18}$ alkenyl, or said alky or said alkenyl substituted by —Cl, by —ZCN, by —NCZ or by —CN, and E is Na, K or —$NR^7R^8R^9$ where $R^7$, $R^8$ and $R^9$ are the same or different and have the same definition as $R^5$.

2. A lubricant composition according to claim 1, wherein A and G in formula I are the same or different and represent

wherein $R^1$ and $R^2$ are the same or different and are $C_1$-$C_{24}$ alkyl or said alkyl substituted by —Cl, —$ZR^5$, —ZCN, —NCZ, —$CZZ^1R^5$, —$ZCZ^1R^5$, —$CZNR^7R^8$, —$NR^7R^8$ or —$CZZ^1E$, where Z, $Z^1$, $R^5$, $R^7$, $R^8$ and E are defined in claim 1.

3. A lubricant compostion according to claim 1, wherein A and G in formula I are the same or different and represent

wherein $R^1$ and $R^2$ are the same or different and represent $C_1$-$C_{18}$ alkyl or said alkyl substituted by —Cl, —$ZR^5$, ZCN, —NCZ, —$CZZ^1R^5$, —$NR^7R^8$, —$ZCZ^1R^5$, —$CZNR^7R^8$ or $CZZ^1E$, where $R^5$ has the same definition as $R^1$ and $R^2$ and where Z, $Z^1$, $R^7$, $R^8$ and E are defined in claim 11.

4. A lubricant composition according to claim 1, wherein A and G in formula I are the same or different and represent

wherein $R^1$ and $R^2$ are the same or different and represent $C_1$-$C_{18}$ alkyl.

5. A lubricant composition according to claim 4, wherein A and G in formula I represent

wherein $R^1$ and $R^2$ are the same represent $C_5$-$C_{15}$ alkyl.

6. A lubricant composition according to claim 1, wherein n in formula I is 2.

7. A lubricant composition which comprises
(a) a mineral oil, a synthetic oil or mixture thereof, and (b) 0.001 to 5% by weight, based on the lubricant, of one or more compounds of formula I

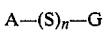

(I)

wherein n is an integer from 2 to 6, and represents

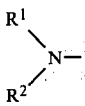

wherein $R^1$ and $R^2$ are the same or different and are $C_1$-$C_{24}$ alkyl, $C_3$-$C_{18}$ alkenyl, $C_3$-$C_{12}$ cycloalkyl, aryl containing 6 to 10 carbon atoms in the nucleus, $C_7$-$C_{30}$ aralkyl, or said alkyl, said alkenyl, said cycloalky, said aryl or said aralkyl substituted by —Cl, by —$ZR^5$, by —ZCN, by —NCZ, by $CZZ^1R^5$, by —$ZCZ^1R^5$, by —$CZNR^7R^8$, by —$NR^7R^8$ or by —$CZZ^1E$, where Z and $Z^1$ are independently —O—, —S—, —$S_2$—, —SO—, —$SO_2$— or —$SO_3$—, $R^5$ is hydrogen, $C_1$-$C_{18}$ alkyl, $C_3$-$C_{18}$ alkenyl, or said alkyl or said alkenyl substituted by —Cl, by —ZCN, by —NCZ or by —CN, and E is Na, K or —$NR^7R^8R^9$ where $R^7$, $R^8$, and $R^9$ are the same or different and have the same definition as $R^5$, and G represents morpholino, piperazino, piperidino, pyrrolidino, hexamethyleneimino, imidazolidino or pyrrolo.

8. A lubricant composition according to claim 7, wherein A in formula I represents

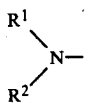

wherein $R^1$ and $R^2$ are the same or different and are $C_1$-$C_{24}$ alkyl or said alkyl substituted by —Cl, —$ZR^5$, —ZCN, —NCZ, —$CZZ^1R^5$, —$ZCZ^1R^5$, —$CZNR^7R^8$, —$NR^7R^8$ or —$CZZ^1E$, where Z, $Z^1$, $R^5$, $R^7$, $R^8$ and E are defined in claim 7.

9. A lubricant composition according to claim 7 wherein G in formula I is morpholino.

10. A lubricant composition according to claim 7, wherein A in formula I represents

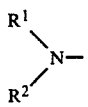

wherein $R^1$ and $R^2$ are the same or different and represent $C_1$-$C_{18}$ alkyl or said alkyl substituted by —Cl, —$ZR^5$, ZCN, —NCZ, —$CZZ^1R^5$, —$NR^7R^8$, —$ZCZ^1R^5$, —$CZNR^7R^8$ or $CZZ^1E$, where $R^5$ has the same definition as $R^1$ and $R^2$ and where Z, $Z^1$, $R^7$, $R^8$ and E are defined in claim 7.

11. A lubricant composition according to claim 7 wherein n in formula I is 2.

* * * * *

UNITED STATES PATENT AND TRADEMARK OFFICE
CERTIFICATE OF CORRECTION

PATENT NO. : 4,482,463
DATED : November 13, 1984
INVENTOR(S) : Henri Dubas and Rudolf Kirchmayr It is certified that error appears in the above-identified patent and that said Letters Patent is hereby corrected as shown below:

Claim 1, Column 7, Line 4 should read-- alkenyl, or said alkyl or said alkenyl substituted by --.

Claim 7, Column 8, Line 8 should read--

A represents --.

Claim 7, Column 8, Line 18 should read-- aralkyl, or said alkyl, said alkenyl, said cycloalkyl, said --.

Signed and Sealed this

First Day of October 1985

[SEAL]

Attest:

DONALD J. QUIGG

Attesting Officer

Commissioner of Patents and
Trademarks—Designate